(12) United States Patent
Morvan et al.

(10) Patent No.: US 8,933,279 B2
(45) Date of Patent: Jan. 13, 2015

(54) METHOD FOR PREPARING A MIXTURE OF ALCOHOLS

(71) Applicant: Rhodia Operations, Aubervilliers (FR)

(72) Inventors: Didier Morvan, Mornant (FR); Loic Baussaron, Venissieux (FR); Gerald Bocquenet, Communay (FR); Roland Jacquot, Francheville (FR); Philippe Marion, Vernaison (FR); Virginie Belliere-Baca, Andresy (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 14/348,709

(22) PCT Filed: Oct. 2, 2012

(86) PCT No.: PCT/EP2012/069478
§ 371 (c)(1),
(2) Date: Mar. 31, 2014

(87) PCT Pub. No.: WO2013/050376
PCT Pub. Date: Apr. 11, 2013

(65) Prior Publication Data
US 2014/0235902 A1      Aug. 21, 2014

(30) Foreign Application Priority Data
Oct. 3, 2011  (FR) .................................... 11 58913

(51) Int. Cl.
*C07C 31/02* (2006.01)
*C07C 29/34* (2006.01)
*C07C 29/17* (2006.01)
*C07C 29/80* (2006.01)

(52) U.S. Cl.
CPC ............... *C07C 29/17* (2013.01); *C07C 29/172* (2013.01); *C07C 29/175* (2013.01); *C07C 29/34* (2013.01); *C07C 29/80* (2013.01)
USPC ......................... 568/902.2; 568/903; 568/913

(58) Field of Classification Search
CPC ..... C07C 29/34; C07C 29/175; C07C 29/172; C07C 29/80
USPC ....................................... 568/902.2, 903, 913
See application file for complete search history.

(56) References Cited

U.S. PATENT DOCUMENTS

| 2007/0255079 A1 | 11/2007 | Tsuchida et al. |
| 2009/0205246 A1 | 8/2009 | Tsuchida et al. |

FOREIGN PATENT DOCUMENTS

| EP | 2206763 A1 | 7/2010 |
| WO | WO 2013092399 A1 | 6/2013 |
| WO | WO 2013092789 A1 | 6/2013 |

OTHER PUBLICATIONS

Tsuchida, Takashi, et al—"Reaction of ethanol over hydroxyapatite affected by Ca/P ratio of catalyst", 2008, Journal of Catalysis, vol. 259, pp. 183-189, Academic Press, Duluth, MN, Elsevier, XP 025496829; 7 pgs.
U.S. Appl. No. 14/366,281, filed Jun. 18, 2014, Virginie Belliere-Baca, et al.
U.S. Appl. No. 14/366,285, filed Jun. 18, 2014, Didier Morvan, et al.

*Primary Examiner* — Sikarl Witherspoon
(74) *Attorney, Agent, or Firm* — Beatrice C. Ortego

(57) ABSTRACT

A method for preparing a mixture (M) comprising at least an alcohol (Aj), said method comprising the following steps: i) a step in which at least an alcohol (Ai) in gaseous state is oligomerized, thereby producing a mixture (A); ii) a step in which the mixture (A) is condensed to a gaseous stream and to a liquid stream corresponding to a condensed mixture (A); and iii) a step in which the condensed mixture (A) is hydrogenated in the liquid state.

20 Claims, No Drawings

METHOD FOR PREPARING A MIXTURE OF ALCOHOLS

The present application is a U.S. national stage entry under 35 U.S.C. §371 of International Application No. PCT/EP2012/069478 filed Oct. 2, 2012, which claims priority to French Application No. 11.58913 filed on Oct. 3, 2011, the whole content of this application being herein incorporated by reference for all purposes.

The present invention relates to a process for the preparation of a mixture of alcohols.

Industrially, the most important alcohols are ethanol, 1-propanol, n-butanol, alcohols for plasticizers exhibiting a $C_6$-$C_{11}$ alkyl chain and fatty alcohols exhibiting a $C_{12}$-$C_{18}$ alkyl chain used as detergents. These different alcohols are prepared from fossil resources, either by the Oxo route from olefins or by the Ziegler process (trialkylaluminum oxidation) (K. Ziegler et al., Justus Liebigs Ann. Chem., 629 (1960), 1). Alcohols are also used as solvents, as diluents for paints (mainly light alcohols exhibiting a $C_1$-$C_6$ alkyl chain) or as intermediates resulting in esters, but also as organic compounds, as lubricants or as fuels.

The synthesis of these alcohols often takes place in several stages and results in mixtures of alcohols. For example, the alcohols exhibiting a $C_6$ alkyl chain are synthesized by codimerization of butene and propene, then converted into a mixture of aldehydes by hydroformylation, before being hydrogenated, in order to finally result in a mixture of alcohols exhibiting a $C_6$ alkyl chain. For example, butanol has to date been produced very largely by the process of hydroformylation of propylene, a petroleum derivative (Wilkinson et al., *Comprehensive Organometallic Chemistry, The Synthesis, Reactions and Structures of Organometallic Compounds*, Pergamon Press, 1981, 8). Butanol can also be obtained by fermentation processes which have become topical with the rise in petroleum starting materials. Acetone-butanol-ethanol fermentation, better known under the name of ABE fermentation, coproduces a mixture of ethanol, acetone and butanol in a ratio by weight of approximately 1/3/6. The source bacterium of the fermentation belongs to the family of the *Clostridium acetobutylicum* bacteria.

Given the diversity of the alcohols needed by the chemical industry and the broad range of use, there thus exists a need to set up a simplified process for the formation of alcohols resulting in good yields (and minimizing mixtures). It is also advantageous to have a flexible process which makes it possible to use ethanol resulting from renewable materials to form heavier biosourced alcohols.

It is an aim of the present invention to provide a process comprising a simplification of the stage of separation of the alcohols formed.

Another aim of the invention is to prepare a mixture of alcohols devoid of noncondensable gases.

Another aim of the present invention is to provide a process for obtaining a mixture of alcohols which is devoid of aldehyde and in particular of acetaldehyde.

Furthermore, an aim of the invention is to provide a process which makes it possible to stabilize the reaction medium.

Another aim of the present invention is to provide a process for the preparation of alcohols and in particular butanol which is easy to carry out and which results in a better overall yield of the reaction.

A subject matter of the present invention is thus a process for the preparation of a mixture (M) comprising at least one alcohol (Aj), said process comprising the following stages:
i) a stage of oligomerization of at least one alcohol (Ai) in the gas phase, resulting in a mixture (A);
ii) a stage of condensation of the mixture (A), resulting in a gas stream and in a liquid stream corresponding to a condensed mixture (A); and
iii) a stage of liquid-phase hydrogenation of the condensed mixture (A).

In the context of the invention and unless otherwise mentioned, the term "mixture (A)" is understood to mean a mixture resulting from stage i) of oligomerization of at least one alcohol (Ai) in the gas phase. The mixture (A) thus represents a gas mixture at the reaction temperature.

In the context of the invention and unless otherwise mentioned, the term "condensed mixture (A)" is understood to mean a mixture (A) which has been subjected to a stage ii) of condensation on conclusion of stage i). The condensed mixture (A) constitutes the mixture subjected to stage iii) of liquid-phase hydrogenation.

In the context of the invention and unless otherwise mentioned, the term "alcohols (Ai)" is understood to mean alcohols for which the linear or branched alkyl chain comprises n carbon atoms, with n representing an integer from 1 to 10. According to the invention, the term "alcohols (Ai)" also encompasses the term "starting alcohols". The "alcohols (Ai)" according to the invention can, for example, be: methanol, ethanol, propanol, butanol, pentanol, hexanol, heptanol, octanol, nonanol or decanol. The alcohols (Ai) denote the starting alcohols before the oligomerization stage.

In the context of the invention and unless otherwise specified, the term "alcohols (Aj)" is understood to mean alcohols for which the linear or branched alkyl chain comprises m carbon atoms, with m representing an integer from 2 to 20. According to the invention, the term "alcohols (Aj)" also encompasses the term "alcohols formed" or also "economically upgradable alcohols". The "alcohols (Aj)" according to the invention can, for example, be ethanol, butanol, hexanol, octanol, decanol, 2-ethylbutanol and 2-ethylhexanol.

In the context of the invention, the alcohols (Aj) are obtained by oligomerization of one or more alcohols (Ai).

In the context of the invention and unless otherwise mentioned, the term "oligomerization of an alcohol" is understood to mean a process for conversion of a monomeric alcohol into an oligomeric alcohol. According to the invention, the oligomerization can, for example, be a dimerization.

Preferably, the alcohol (Ai) is ethanol.

According to a specific embodiment, the oligomerization is a dimerization, preferably a dimerization of ethanol. In this embodiment, the mixture (M) obtained comprises butanol.

According to a specific embodiment, the present invention relates to a process for the preparation of a mixture (M) comprising butanol, said process comprising the following stages:
i) a stage of oligomerization, in particular of dimerization, of ethanol in the gas phase, resulting in a mixture (A);
ii) a stage of condensation of the mixture (A), resulting in a gas stream and in a liquid stream corresponding to the condensed mixture (A); and
iii) a stage of liquid-phase hydrogenation of the condensed mixture (A).

Typically, the stage of oligomerization, in particular of dimerization, in the gas phase can be carried out using any reactor generally known to a person skilled in the art.

According to the invention, the alcohol(s) (Ai) used can be anhydrous or aqueous. If the alcohol(s) (Ai) used is (are) aqueous, it (they) can comprise from 0.005% to 20% by weight of water, with respect to the total weight of alcohol(s) (Ai).

According to one aspect of the invention, stage i) of oligomerization, in particular dimerization, of the process can be carried out in the presence of a solid acid/base catalyst. Preferably, the catalyst is of alkaline earth metal phosphate type. More particularly, the catalyst is chosen from the catalysts of the family of the calcium hydroxyapatites (HAPs), of general formula $Ca_{10-z}(HPO_4)_z(PO_4)_{6-z}(OH)_{2-z}$ with $0<z\leq 1$.

According to one embodiment, when the catalyst is chosen from calcium hydroxyapatites, the (Ca+M)/P molar ratio (with Ca representing calcium, P representing phosphorus and M representing a metal) is from 1.5 to 2, preferably from 1.5 to 1.8 and preferentially from 1.6 to 1.8. According to the invention, M can represent a metal or a metal oxide, ranging from 0 mol % to 50 mol % of replacement of the calcium, in particular from 0 mol % to 20 mol %, and can be chosen from Li, Na, K, Rb, Cs, Sc, Y, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb and Yb.

According to the invention, stage i) of the process can be carried out at a temperature of from 100° C. to 500° C., preferably from 200° C. to 450° C. and preferentially from 300° C. to 450° C. In particular, the temperature is from 350° C. to 425° C. and more particularly from 375° C. to 425° C.

According to the invention, stage i) can be carried out at a pressure of from 0.3 to 6 bar absolute and preferably from 0.8 to 5 bar absolute.

In stage i) of the process of the invention, one or more alcohols (Ai), in particular ethanol, can be fed in the vapor phase. The flow rate of alcohol(s) (Ai) of said stage i) is from 1 to 10 g of alcohol (Ai), preferably from 1 to 8, preferentially from 1 to 6 and more preferably still from 1 to 5 per hour per g of catalyst. In particular, the flow rate of alcohol(s) (Ai) is from 2 to 6 g of alcohol(s) (Ai) per hour per g of catalyst.

In the context of the invention and unless otherwise mentioned, the term "productivity" is understood to mean the measurement of the effectiveness of the process. The productivity according to the invention corresponds to the amount of an alcohol (Aj), in particular butanol, produced per hour per one gram of catalyst used in the process.

In the context of the invention and unless otherwise mentioned, the term "yield" is understood to mean the ratio, expressed as percentage, of the amount of product obtained to the theoretical amount desired.

In the context of the invention and unless otherwise mentioned, the term "selectivity" is understood to mean the number of moles of alcohol (Ai) and in particular of ethanol converted into a desired product with respect to the number of moles of alcohol (Ai) converted.

According to the invention, stage i) in the gas phase (vapor phase) can result in a mixture (A) comprising in particular from 1% to 30% by weight of reducible products, regarded as reaction intermediates.

In the context of the invention and unless otherwise mentioned, the term "reducible product" is understood to mean a compound which can be reduced during the hydrogenation stage iii), such as an alkene, an alkyne, an aldehyde or a ketone. According to the invention, the reducible products can, for example, be acetaldehyde, crotonaldehydes (cis and trans), crotyl alcohols (cis and trans), buten-1-ol, butadiene, butanal, hexenols and hexanal.

According to the invention, the mixture (A) is subjected, on conclusion of stage i) and before stage iii), to a stage of condensation of the mixture (A) (stage ii), resulting in a gas stream and in a condensed mixture (A) corresponding to a liquid stream. This stage makes it possible to carry out the liquid-phase hydrogenation reaction.

According to another aspect of the invention, the condensed mixture (A) can be subjected, on conclusion of stage ii) and before stage iii), to a stage of separation of the liquid/gas streams, in order to remove the gas stream.

According to the invention, the additional stage of separation of the liquid/gas streams can be carried out on the condensed mixture (A), in order to remove the gas stream and the not economically upgradable light constituents. This stage advantageously makes it possible to be freed from the noncondensable gases.

In the context of the invention and unless otherwise mentioned, the term "noncondensable gas" is understood to mean a gas which cannot be condensed to give a liquid phase, at a temperature greater than 20° C. at atmospheric pressure. According to the invention, the noncondensable gases can, for example, be carbon monoxide, butene, ethylene, hexene, butane, carbon dioxide, hydrogen and ethane.

Thus, the process according to the invention advantageously makes it possible to obtain a better lifetime of the catalyst of the hydrogenation reaction. This is because the process according to the invention, comprising a stage ii) of condensation of the reaction mixture (A) on exiting from oligomerization, in particular from dimerization, (on conclusion of stage i) and of separation of the liquid/gas streams, makes it possible to separate the noncondensable gases from the liquid phase to be hydrogenated (stage iii). In point of fact, these noncondensable gases comprise in particular not insignificant amounts of carbon monoxide (CO), up to 130 ppm, which is a poison for the hydrogenation catalysts conventionally used industrially, such as nickel.

This separation also makes it possible to prevent the coking of the hydrogenation catalyst often due to carbon-comprising noncondensable entities of the ethane, ethylene, hexene, butane or butadiene type. This is because some of these entities have a tendency to polymerize.

This separation also makes possible a saving in hydrogen since the unsaturated entities, in particular butadiene, ethylene or hexene, present in the gas stream are not hydrogenated.

According to one embodiment, the mixture (A) obtained on conclusion of stage i) is cooled to a temperature of between 0° C. and 100° C., in order to condense and separate the various constituents of said mixture (A). The cooling can be carried out using a technique well known to a person skilled in the art, such as a heat exchanger of shell-and-tube type or a plate exchanger. On conclusion of the stage of condensation ii) of the mixture (A), a vapor stream (gas stream) and a liquid stream (condensed mixture (A)) are obtained.

According to the invention, the vapor stream and the condensed mixture (A) can be separated in one or more simple liquid/vapor separators operating at increasingly low temperatures, including heat exchangers, in a distillation column or in both of these types of appliance in series.

On conclusion of the separation stage, two streams can be obtained, a gas stream preferably comprising at least one alcohol (Ai), in particular ethanol, and gases, such as hydrogen, ethane, ethylene or butene, and a liquid stream comprising the remaining unconverted alcohol(s) (Ai), the water resulting from the reaction and also the economically upgradable alcohols (Aj).

According to the invention, the process can comprise a stage of washing the gas stream obtained on conclusion of the separation stage. The washing stage can be carried out in an absorber in order to recover the alcohol(s) (Ai) present, in particular ethanol, and also acetaldehyde entrained in the gas stream resulting from the separation stage.

According to one embodiment, this stage of washing by absorption can be carried out in a washing column operating at the lowest possible temperature, from 0° C. to 50° C., according to the cold sources available, and at the same pressure as stage i) (apart from the pressure losses). It can be carried out with water devoid of alcohols (Ai) and in particular devoid of ethanol or by using alcohols (Aj) produced later in the process.

The gas stream resulting from the washing stage is advantageously purified so as to recover the hydrogen present in said gas stream for the purpose of using it in the hydrogenation stage iii). In particular, the hydrogen can be purified by a pressure swing adsorption (PSA) mechanism, by use of a porous membrane, by absorption or by cryogenics.

According to another form of the invention, the condensed mixture (A), optionally having been subjected to an additional stage of separation, is subjected to a stage iii) of liquid-phase hydrogenation. More specifically, the alcohol(s) (Ai), employed in said stage i) of the process according to the invention, present in said condensed mixture (A) and which has (have) not reacted, for example ethanol, is (are) advantageously separated from the alcohol(s) (Aj) also present in said condensed mixture (A) by liquid/liquid separation, prior to carrying out said stage iii). According to this embodiment, said condensed mixture (A) is preferably subjected to at least one distillation stage, so as to obtain at least one first liquid stream comprising, preferably composed of, the alcohol(s) (Ai) which has (have) not reacted during the implementation of said stage i) of the process according to the invention and a second liquid stream comprising, preferably composed of, the alcohol(s) (Aj). In accordance with said embodiment, the alcohol(s) (Ai) extracted from said condensed mixture (A) are advantageously directly economically upgradable, for example in order to be introduced into fuel bases.

According to one embodiment, the condensed mixture (A) resulting from stage ii) can be brought back to a temperature of less than 165° C. by a technology well known to a person skilled in the art, such as an exchanger of shell-and-tube type or a plate exchanger.

According to the invention, the liquid-phase hydrogenation stage is carried out at a temperature of less than or equal to 165° C. In particular, the temperature is from 50° C. to 165° C., preferably from 60° C. to 162° C. and preferentially from 80° C. to 160° C.

According to the invention, the condensed mixture (A) is subsequently brought into contact with a hydrogen flow sufficient to hydrogenate the reducible products. According to the invention, the hydrogen flow can be from 0.48 to 240 $l/g_{alcohol(Ai)}/g_{catalyst}$ and preferably from 1.5 to 48 $l/g_{alcohol(Ai)}/g_{catalyst}$ under standard temperature and pressure conditions.

According to one embodiment, the liquid-phase hydrogenation stage is carried out at a pressure of greater than or equal to 10 bar. In particular, the pressure is from 10 to 50 bar, preferably from 12 to 45 bar and preferentially from 15 to 40 bar.

According to the invention, the hydrogen used in said stage iii) originates from said gas stream purified according to one of the methods described above and/or from a process for the production of hydrogen employing a hydrocarbon or an alcohol, such as ethanol.

According to the invention, the liquid-phase hydrogenation stage can be carried out in the presence of a metal catalyst chosen from the group consisting of Fe, Ni, Co, Cu, Cr, W, Mo, Pd, Pt, Rh and Ru, it being possible for said catalyst optionally to be supported. Mention may be made, as support, of alumina, celite, zirconium dioxide, titanium dioxide or silica. Preferably the optionally supported catalyst used is chosen from the group consisting of Ni, Co, Cu, Pd, Pt, Rh and Ru. The catalyst can be of the Raney nickel type.

According to the invention, the metals can be used alone or as a mixture.

Typically, the liquid-phase hydrogenation stage can be carried out using any reactor generally known to a person skilled in the art.

According to one embodiment, the liquid-phase hydrogenation stage can be carried out in an isothermal or adiabatic and tubular or multitubular fixed bed reactor, or a catalyst-coated reactor/exchanger, or a reactor stirred by a self-suction stirrer, or an ejector of venturi or tubular type.

According to the invention, the catalyst used in stage iii) can be immobilized, in the form of grains or extrudates or in the form of a metal foam.

According to the invention, the catalyst used in stage iii) can be in the form of fine particles.

According to the invention, two different appliances can be envisaged in carrying out the hydrogenation stage:
a) one in which the catalyst can be immobilized in a reactor in the form of grains or extrudates or supported on a metal foam. The reactor associated with this type of catalyst is preferably an isothermal or adiabatic and tubular or multitubular fixed bed or a catalyst-coated reactor/exchanger, operated in trickling or immersed mode;
b) the other in which the catalyst can be in the form of fine particles (from 5 to 100 μm in diameter) in suspension in the liquid phase. The preferred reactor for this type of catalyst can be chosen from the group of reactors stirred by a self-suction stirrer or an ejector of venturi or tubular type.

Typically, in this type of appliance, the catalyst subsequently has to be separated by a suitable technology of tangential filter or decanter type.

Preferably, the liquid-phase hydrogenation stage is carried out in an appliance of type a) described above.

According to the invention, the mixture (M) obtained on conclusion of the hydrogenation stage is devoid of the intermediate entities obtained on conclusion of stage i), such as alcohologens, for example crotyl alcohols (cis and trans), butanal, buten-1-ol, hexanal or crotonaldehydes (cis and trans), or hexenols, which were reduced in the form of economically upgradable products. The hydrogenation stage can thus make possible an increase in the yield of the reaction with regard to all the different alcohols (Aj) generated.

According to the invention, the mixture (M) obtained is devoid of aldehyde entities and in particular is devoid of acetaldehyde, which makes possible better stability over time of said mixture (M).

According to the invention, the mixture (M) can comprise the remaining unconverted alcohol(s) (Ai) and in particular ethanol, water resulting from the reaction and/or originating from fresh alcohol(s) (Ai), and alcohols (Aj), in particular butanol.

According to a specific embodiment, the mixture (M) obtained according to the process can comprise at least 5% (by weight, with respect to the total weight of the mixture (M)) of butanol, preferably at least 8% and preferentially at least 10% of butanol.

In the context of the invention and unless otherwise mentioned, the term "fresh alcohol (Ai)" is understood to mean the alcohol (Ai) used as starting reactant in the oligomerization reaction. According to the invention, the fresh alcohol (Ai) differs from the recycling alcohol (Ai).

In accordance with the process according to the invention, said mixture (M) preferably comprises several alcohols (Aj) for which the linear or branched alkyl chain comprises m carbon atoms, with m representing an integer equal to 2 or from 2 to 20. Preferably, said mixture (M) comprises at least butanol (m=4). According to another aspect of the invention, the mixture (M) comprises, in addition to butanol, other alcohols (Aj) for which the linear or branched alkyl chain comprises m carbon atoms, with m representing an integer equal to 2 or from 2 to 20. More particularly, the mixture (M) can comprise, in addition to butanol, linear alcohols, such as hexanol, octanol or decanol, or branched alcohols, such as 2-ethylbutanol or 2-ethylhexanol.

According to one aspect of the invention, the process can comprise, on conclusion of stage iii), successive distillation stages, in order to separate the different economically upgradable alcohols of the mixture (M), and also stages of recycling alcohol(s) (Ai), in particular ethanol.

More particularly, the mixture (M), comprising the remaining unconverted alcohol(s) (Ai), in particular ethanol, the water resulting from the reaction and/or originating from fresh alcohol(s) (Ai), and the economically upgradable alcohols, can be separated in an assembly of distillation columns intended to recover the economically upgradable alcohols, to remove the water resulting from the reaction and the water resulting from fresh alcohol(s) (Ai) (in the case where the alcohol(s) (Ai) used for the oligomerization is (are) aqueous) and to recycle the unconverted alcohol(s) (Ai) of the reaction, generally in their azeotropic form.

According to one embodiment, the mixture (M) resulting from the hydrogenation under pressure can be reduced in pressure to a pressure which makes it possible to carry out the separation of the water/alcohol(s) (Ai) azeotrope and the economically upgradable alcohols.

In the context of the invention and unless otherwise mentioned, the term "pressure-reduced mixture (M)" is understood to mean a mixture (M) which has been reduced in pressure on conclusion of the hydrogenation stage.

According to the invention, the pressure-reduced mixture (M) resulting from the hydrogenation can be sent to an assembly of two distillation columns denoted C1 and C2, interlinked in order to obtain three streams:

F1: the water/alcohol(s) (Ai) azeotrope and in particular the water/ethanol azeotrope, which is recycled;
F2: the water resulting from fresh alcohol(s) (Ai) and also the water resulting from the reaction; and
F3: the alcohols (Aj), in particular butanol.

According to one embodiment, the columns C1 and C2 can be plate columns or packed columns.

The presence of the water/alcohol(s) (Ai) azeotrope and in particular of the water/ethanol azeotrope makes it difficult to remove the reaction water. In order to facilitate this separation, the phenomenon of phase separation of the alcohol(s) (Aj)/water mixtures can be used. During the distillation in order to obtain the alcohols (Aj) (F3) at the bottom and the water/alcohol(s) (Ai) azeotrope (F1) at the top, a phase separation can occur in order to generate two liquid phases in equilibrium, a phase rich in alcohol(s) (Aj) and a phase rich in water. This phenomenon can be used to facilitate the separation of various constituents. The feeding can be carried out in the column C1 at the stage which makes it possible to optimize the performance of the assembly.

According to the invention, a decanter can be installed in the bottom part of the column C1, below the feed plate which separates these two liquid phases, or the decanter can be installed inside or outside the column C1. The organic phase, rich in alcohol(s) (Aj), can be recycled as internal reflux of the column C1 and makes it possible to obtain the mixture of alcohols (Aj) at the bottom of this column C1. The aqueous phase can exit from the column C1 and be sent to a column C2 which can be a reflux separation column or a simple stripper. This column C2 can be boiled out and can make it possible to obtain, at the bottom, a stream of water devoid of alcohols (Ai) and (Aj) and in particular devoid of ethanol and butanol.

According to the invention, the distillate from the column C2 can preferably be in the vapor form, this column operating at the same pressure as the column C1. The vapor phase from this column C2 can be returned to the column C1, preferably at the stage above the stage of the liquid/liquid decanter. The top of the column C1 is conventional and can comprise a condenser which makes it possible to obtain the reflux necessary for the separation. The water/alcohol(s) (Ai) azeotrope (F1) and in particular the water/ethanol azeotrope can then be obtained at the top. It can be obtained in the vapor phase or in the liquid phase. If it is obtained in the vapor phase, this prevents having to vaporize it before feeding the synthesis reaction, which advantageously makes it possible to reduce the energy consumption necessary.

According to the invention, the alcohols (Aj) (F3) are obtained at the bottom of the column C1. They can be separated by simple distillation in an additional column C3 in order to obtain the pure butanol at the top and the other alcohols (Aj) different from the butanol at the bottom.

The different alcohols (Aj) can subsequently be separated by successive distillations in order to obtain these different alcohols in the order of their boiling points. The separation of the alcohols by distillation can also be carried out by the dividing wall column (DWC) distillation technology.

According to one embodiment, the fresh alcohol (Ai) and in particular the fresh ethanol, pure or comprising water and also the recycling alcohol (Ai) and in particular the recycling ethanol, if it is liquid, can be vaporized and then superheated up to the reaction temperature before entering a reactor where the oligomerization takes place (oligomerization reactor). If the recycling alcohol (Ai), in particular the recycling ethanol, is in the vapor form, the fresh alcohol (Ai) and in particular the fresh ethanol can be vaporized and then superheated up to the reaction temperature before entering the oligomerization reactor.

The process according to the invention advantageously makes possible an increase in the overall yield of the reaction, a simplification of the stage of separation of the alcohols (Aj) formed and a stabilization in the reaction medium.

The liquid-phase hydrogenation stage advantageously makes possible a better selectivity than a process comprising a gas-phase hydrogenation stage. This is because the gas-phase hydrogenation of the batches resulting from an oligomerization and in particular a dimerization of alcohol(s) (Ai) and in particular of ethanol over acid/base catalysts is not complete; there remain in particular aldehydes, such as acetaldehyde, as was observed in the application EP 2 206 763. This is due to a thermodynamic balance. In point of fact, acetaldehyde is not an economically upgradable product and causes separation problems. This is because the separation of ethanol and acetaldehyde is difficult as an azeotrope exists.

It has been found that, by hydrogenating these batches in the liquid phase, a complete reduction of all the entities, including acetaldehyde, which forms ethanol, is obtained. Thus, the process according to the invention makes it possible to facilitate the separations insofar as the mixture comprises one entity less to be separated and there exist fewer acetaldehyde/alcohols binary mixtures. The ethanol formed from the acetaldehyde according to the invention can subsequently be reinjected into the process. This has the effect of lowering the conversion of the ethanol and thus of increasing the selectivities and the yields of economically upgradable alcohols and in particular butanol. Thus, the liquid-phase hydrogenation stage makes it possible to improve the overall selectivity and efficiency of the process. Furthermore, the liquid-phase hydrogenation is advantageous as it makes it possible to stabilize the mixture over time, due to the absence of the aldehyde entities.

The liquid-phase hydrogenation stage is advantageous in reducing the sizing of the process. This is because a liquid-phase hydrogenation makes it possible to use lesser amounts of hydrogen and catalyst than for a gas-phase hydrogenation (for which a molar excess of $H_2$ is necessary), while retaining a high efficiency.

The following examples illustrate the invention without, however, limiting it.

EXAMPLES

Example 1

Liquid-Phase Hydrogenation with Ni (HTC) Catalyst at 130° C.

3.1 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 390° C. and the pressure was 1 bar absolute. A liquid phase was recovered after condensing the mixture at 10° C. at the reactor outlet. The hydrogenation was carried out on a batch of 200 g of the liquid phase collected previously in an autoclave under a pressure of 30 bar of hydrogen, at 130° C. for 30 minutes, with 2 g of alumina-supported nickel catalyst from the supplier Johnson Matthey (Ni HTC 500, extrudates of 1.2 mm comprising 21% by weight of nickel), activated according to the recommendations of the supplier. The mixture resulting from this hydrogenation stage was injected, after filtration, into a gas chromatograph (GC Agilent HP6890N, HP-innowax (PEG) 30 m×0.25 mm×0.25 μm column, FID detector, cyclohexanol internal standard).

The conversion of the ethanol is 31.2%. The percentages by weight of the different quantified products are as follows:
Butanol: 16%
Diethyl ether: 0.2%
Ethylbutanol: 1.4%
Hexanol: 1.8%
Ethylhexanol: 0.3%
Octanol: 0.25%
Xylene: 0.08%
Acetaldehyde: 0%
Crotyl alcohol and isomers: 0%
Hexen-1-ol: 0%
Butanal: 0%
Crotonaldehyde: 0%
Hexanal: 0%

Thus, a butanol yield of 19.6% and a productivity of 0.34 g of butanol per hour and per g of catalyst were obtained. No trace of aldehydes or of unsaturations was detected, which confirms that the hydrogenation was total.

Example 2

Liquid-Phase Hydrogenation with Powdered Ni (HTC) Catalyst at 120° C.

5.35 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 400° C. and the pressure was 1 bar absolute. A liquid phase was recovered after condensing the mixture at 10° C. at the reactor outlet. The hydrogenation was carried out on a batch of 200 g of the liquid phase collected previously in an autoclave under a pressure of 30 bar of hydrogen, at 120° C. for 30 minutes, with 2 g of alumina-supported nickel catalyst ground to a powder from the supplier Johnson Matthey (Ni HTC 500, comprising 21% by weight of nickel), activated according to the recommendations of the supplier. The mixture resulting from this hydrogenation stage was injected, after filtration, into a gas chromatograph (GC Agilent HP6890N, HP-innowax (PEG) 30 m×0.25 mm×0.25 μm column, FID detector, cyclohexanol internal standard).

The conversion of the ethanol is 25.5%. The percentages by weight of the different products are as follows:
Butanol: 13.9%
Diethyl ether: 0.1%
Ethylbutanol: 1%
Hexanol: 1.4%
Ethylhexanol: 0.2%
Octanol: 0.17%
Xylene: 0.06%
Acetaldehyde: 0%
Crotyl alcohol and isomers: 0%
Hexen-1-ol: 0%
Butanal: 0%
Crotonaldehyde: 0%
Hexanal: 0%

Thus, a butanol yield of 17% and a productivity of 0.51 g of butanol per hour and per g of catalyst were obtained. No trace of aldehydes or of unsaturations was detected; the hydrogenation was total. Furthermore, it was noted that 100% of the weight charged was recovered; there was thus no cracking of the material to give CO and methane.

Example 3

Liquid-Phase Hydrogenation with Ni (HTC) Catalyst at 120° C., Dimerization Resulting from a Different Ca/P Ratio 5.65 ml/min of 95% by weight (water q.s. for 100%) ethanol were fed to a reactor (height of 80 cm, diameter of 2.8 cm) containing 72 g of calcium hydroxyapatite (Ca/P ratio=1.685) (supplier: Sangi). The reaction temperature was 400° C. and the pressure was 1 bar absolute. A liquid phase was recovered after condensing the mixture at 10° C. at the reactor outlet. The hydrogenation was carried out on a batch of 200 g of the liquid phase collected previously in an autoclave under a pressure of 30 bar of hydrogen, at 120° C. for 30 minutes, with 2 g of alumina-supported nickel catalyst from the supplier Johnson Matthey (Ni HTC 500, extrudates of 1.2 mm comprising 21% by weight of nickel), activated according to the recommendations of the supplier. The mixture resulting from this hydrogenation stage was injected, after filtration, into a gas chromatograph (GC Agilent HP6890N, HP-innowax (PEG) 30 m×0.25 mm×0.25 μm column, FID detector, cyclohexanol internal standard).

The conversion of the ethanol is 20%. The percentages by weight of the different products are as follows:
Butanol: 10.4%
Diethyl ether: 0.1%
Ethylbutanol: 0.9%
Hexanol: 1%
Ethylhexanol: 0.12%
Octanol: 0.14%
Xylene: 0.06%
Acetaldehyde: 0%
Crotyl alcohol and isomers: 0%

Hexen-1-ol: 0%
Butanal: 0%
Crotonaldehyde: 0%
Hexanal: 0%

Thus, a butanol yield of 17% and a productivity of 0.51 g of butanol per hour and per g of catalyst were obtained. No trace of aldehydes or of unsaturations was detected; the hydrogenation was thus total.

Example 4

Liquid-Phase Hydrogenation with Co (HTC) Catalyst at 130° C.

5.35 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 400° C. and the pressure was 1 bar absolute. A liquid phase was recovered after condensing the mixture at 10° C. at the reactor outlet. The hydrogenation was carried out on a batch of 200 g of the liquid phase collected previously in an autoclave under a pressure of 30 bar of hydrogen, at 130° C. for 30 minutes, with 2 g of alumina-supported cobalt catalyst from the supplier Johnson Matthey (Co HTC 2000, extrudates of 1.2 mm comprising 15% by weight of cobalt), activated according to the recommendations of the supplier. The mixture resulting from this hydrogenation stage was injected, after filtration, into a gas chromatograph (GC Agilent HP6890N, HP-innowax (PEG) 30 m×0.25 mm×0.25 µm column, FID detector, cyclohexanol internal standard).

The conversion of the ethanol is 30.4%. The percentages by weight of the different products are as follows:
Butanol: 15%
Diethyl ether: 0.1%
Ethylbutanol: 1.25%
Hexanol: 1.55%
Ethylhexanol: 0.28%
Octanol: 0.2%
Xylene: 0.06%
Acetaldehyde: 0%
Crotyl alcohol and isomers: 0%
Hexen-1-ol: 0%
Butanal: 0%
Crotonaldehyde: 0%
Hexanal: 0%

Thus, a butanol yield of 18.4% and a productivity of 0.55 g of butanol per hour and per g of catalyst were obtained. No trace of aldehydes or of unsaturations was detected; the hydrogenation was thus total.

Example 5

Liquid-Phase Hydrogenation with Powdered Ni-3354E Catalyst (BASF) at 120° C.

5.35 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 400° C. and the pressure was 1 bar absolute. A liquid phase was recovered after condensing the mixture at 10° C. at the reactor outlet. The hydrogenation was carried out on a batch of 200 g of the liquid phase collected previously in an autoclave under a pressure of 30 bar of hydrogen, at 120° C. for 30 minutes, with 2 g of silica-supported nickel catalyst ground to a powder from the supplier BASF (Ni-3354 E, comprising 60% by weight of nickel), activated according to the recommendations of the supplier. The mixture resulting from this hydrogenation stage was injected, after filtration, into a gas chromatograph (GC Agilent HP6890N, HP-innowax (PEG) 30 m×0.25 mm×0.25 µm column, FID detector, cyclohexanol internal standard).

The conversion of the ethanol is 25.9%. The percentages by weight of the different products are as follows:
Butanol: 13.9%
Diethyl ether: 0.1%
Ethylbutanol: 1%
Hexanol: 1.4%
Ethylhexanol: 0.2%
Octanol: 0.17%
Xylene: 0.06%
Acetaldehyde: 0%
Crotyl alcohol and isomers: 0%
Hexen-1-ol: 0%
Butanal: 0%
Crotonaldehyde: 0%
Hexanal: 0%

Thus, a butanol yield of 17% and a productivity of 0.51 g of butanol per hour and per g of catalyst were obtained. No trace of aldehydes or of unsaturations was detected; the hydrogenation was thus total. It was observed that 100% of the weight charged was recovered; there was thus no cracking of the material to give CO and methane.

Example 6

Liquid-Phase Hydrogenation with Ni (HTC) Catalyst at 160° C.

3.1 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 390° C. and the pressure was 1 bar absolute. A liquid phase was recovered after condensing the mixture at 10° C. at the reactor outlet. The hydrogenation was carried out on a batch of 200 g of the liquid phase collected previously in an autoclave under a pressure of 30 bar of hydrogen, at 160° C. for 30 minutes, with 2 g of alumina-supported nickel catalyst from the supplier Johnson Matthey (Ni HTC 500, extrudates of 1.2 mm comprising 21% by weight of nickel), activated according to the recommendations of the supplier. The mixture resulting from this hydrogenation stage was injected, after filtration, into a gas chromatograph (GC Agilent HP6890N, HP-innowax (PEG) 30 m×0.25 mm×0.25 µm column, FID detector, cyclohexanol internal standard).

The conversion of the ethanol is 30.8%. The percentages by weight of the different products are as follows:
Butanol: 16.2%
Diethyl ether: 0.2%
Ethylbutanol: 1.43%
Hexanol: 1.87%
Ethylhexanol: 0.34%
Octanol: 0.26%
Xylene: 0.1%
Acetaldehyde: 0%
Crotyl alcohol and isomers: 0%
Hexen-1-ol: 0%
Butanal: 0%
Crotonaldehyde: 0%
Hexanal: 0%

Thus, a butanol yield of 19.8% and a productivity of 0.34 g of butanol per hour and per g of catalyst were obtained. No trace of aldehydes or of unsaturations was detected; the hydrogenation was total. In addition, it was observed that 100% of the weight charged was recovered; thus, there was no cracking of the material to give CO and methane (loss of material).

Example 7 (Comparative Example)

Gas-Phase Hydrogenation

This example corresponds to identical amounts to example 6 but with a different hydrogenation appliance suitable for gas phases.

3.1 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 390° C. and the pressure was 1 bar absolute. A liquid phase was recovered after condensing the mixture at 10° C. at the reactor outlet. A gas-phase hydrogenation was carried out, on a batch resulting from this dimerization (378 g), with 16.8 g of 0.5% Pd/SiO$_2$ (by weight) catalyst from the supplier Calcicat (beads with a diameter of 3 to 5 mm) immobilized in a glass reactor (height 20 cm, diameter 2.8 cm) at 150° C. with a hydrogen flow rate of 50 ml/min under atmospheric pressure and a flow rate of liquid to be hydrogenated of 0.55 ml/min.

The conversion of the ethanol is 34%. The percentages by weight of the different products are as follows:
Butanol: 15.43%
Diethyl ether: 0.08%
Ethylbutanol: 1.29%
Hexanol: 1.77%
Ethylhexanol: 0.3%
Octanol: 0.23%
Xylene: 0.06%
Acetaldehyde: 0.84% (corresponding to a selectivity of 2.54%)
Crotyl alcohol and isomers: 0.05%
Hexen-1-ol: 0%
Butanal: 0%
Crotonaldehyde: 0%
Hexanal: 0%

Thus, under gas-phase hydrogenation conditions, 0.84% by weight of acetaldehyde remains after hydrogenation.

Example 8 (Comparative Example)

Gas-Phase Hydrogenation with Another Catalyst and a Different Flow Rate 3.1 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 390° C. and the pressure was 1 bar absolute. A liquid phase was recovered after condensing the mixture at 10° C. at the reactor outlet. A hydrogenation was carried out, on a batch resulting from this dimerization (193 g), with 14.4 g of 13% (by weight) CuO/SiO$_2$ catalyst from the supplier Evonik-Degussa (beads with a diameter of 3 to 5 mm) immobilized in a glass reactor (height 20 cm, diameter 2.8 cm) at 150° C. with a hydrogen flow rate of 100 ml/min under atmospheric pressure and a flow rate of liquid to be hydrogenated of 0.55 ml/min.

The conversion of the ethanol is 31.6%. The percentages by weight of the different products are as follows:
Butanol: 15.18%
Diethyl ether: 0.08%
Ethylbutanol: 1.74%
Hexanol: 1.41%
Ethylhexanol: 0.3%
Octanol: 0.15%
Xylene: 0.06%
Acetaldehyde: 0.79% (a selectivity of 2.57%)
Crotyl alcohol and isomers: 0.06%
Hexen-1-ol: 0%
Butanal: 0%
Crotonaldehyde: 0%
Hexanal: 0%

Thus, under gas-phase hydrogenation conditions, 0.79% by weight of acetaldehyde remains after hydrogenation. In the light of example 7, it was observed that, even on changing the nature of the catalyst and on increasing the hydrogen flow rate, the presence of acetaldehyde remains problematic.

Example 9 (Comparative Example)

Gas-Phase Hydrogenation at a High Temperature 3.1 ml/min of 99.8% by weight (water q.s. for 100%) ethanol were fed to a reactor (height of 80 cm, diameter of 2.8 cm) containing 68 g of calcium hydroxyapatite (Ca/P ratio=1.71) (supplier: Sangi). The reaction temperature was 390° C. and the pressure was 1 bar absolute. A liquid phase was recovered after condensing the mixture at 10° C. at the reactor outlet. A hydrogenation was carried out, on a batch resulting from this dimerization (193 g), with 14.4 g of 13% (by weight) CuO/SiO$_2$ catalyst from the supplier Evonik-Degussa (beads with a diameter of 3 to 5 mm) immobilized in a glass reactor at 180° C. with a hydrogen flow rate of 100 ml/min under atmospheric pressure and a flow rate of liquid to be hydrogenated of 0.55 ml/min.

The conversion of the ethanol is 31.16%. The percentages by weight of the different products are as follows:
Butanol: 15.64%
Diethyl ether: 0.08%
Ethylbutanol: 1.42%
Hexanol: 1.75%
Ethylhexanol: 0.3%
Octanol: 0.22%
Xylene: 0.06%
Acetaldehyde: 0.72% (a selectivity of 2.4%)
Crotyl alcohol and isomers: 0.06%
Hexen-1-ol: 0%
Butanal: 0%
Crotonaldehyde: 0%
Hexanal: 0%

Thus, under gas-phase hydrogenation conditions, 0.79% by weight of acetaldehyde remains after hydrogenation. It was thus observed that, even on increasing the temperature of the gas-phase hydrogenation reaction, acetaldehyde is present and remains problematic.

Simulations were carried out using the Aspen simulation software in order to estimate, under these conditions, the acetaldehyde and hydrogen equilibrium which gives ethanol. With the thermodynamic properties present in the simulator, the hydrogenation under the above conditions of flow rate, composition, pressure and temperature resulted in an acetaldehyde content of 1.3% by weight in the liquid collected for a temperature of 150° C. and a hydrogen flow rate of 50 ml/min, which confirms, to within the calculation and measurement errors, that the hydrogenation of acetaldehyde is not total in the gas phase.

Example 10

Demonstration of the Formation of CO at the Dimerization Outlet 0.47 ml/min of 95% by weight (water q.s. for 100%) ethanol was fed to a reactor (height 12 cm, diameter 1 cm) containing 6 g of calcium hydroxyapatite with a Ca/P ratio=1.67 (supplier: Sangi). The temperature was 400° C. and the pressure was 1 bar absolute.

An ethanol conversion of 25.7% and the following selectivities were observed:

| | |
|---|---|
| BuOH | 45.3 |
| Crotyl alcohols | 4.3 |
| Butanal | 1.2 |
| Crotonaldehyde | 0.4 |
| Ethane | 0.1 |
| $C_2H_4$ | 6.2 |
| Butane | 0.1 |
| $C_4H_8$ | 1.4 |
| 1,3-Butadiene | 10.1 |
| Aromatic compounds | 1.8 |
| Others | 23.5 |
| Acetaldehyde | 5.6 |
| CO | 0.1 |

It should be noted that a selectivity of 0.1% (CO) corresponds to 0.013% (by weight), i.e. 130 ppm of CO in the stream to be hydrogenated. This content is amply sufficient to very rapidly deactivate a hydrogenation catalyst.

Example 11 (Comparative Example)

Cracking During a Gas-Phase Hydrogenation 0.47 ml/min of 95% by weight (water q.s. for 100%) ethanol was fed to a reactor (height 12 cm, diameter 1 cm) containing 6 g of calcium hydroxyapatite with a Ca/P ratio=1.67 (supplier: Sangi). The temperature was 400° C. and the pressure was 1 bar absolute. This dimerization was followed by a hydrogenation with 7.7 g of a commercial Ni HTC (extrudates) catalyst from Johnson Matthey at 150° C. under atmospheric pressure with a hydrogen flow rate of 33 ml/min.

An ethanol conversion of 24.6% and the following selectivities were observed:

| | |
|---|---|
| BuOH | 50 |
| Crotyl alcohols | 0 |
| Butanal | 0.7 |
| Crotonaldehyde | 0 |
| Ethane | 5.3 |
| $C_2H_4$ | 0 |
| Butane | 6.6 |
| $C_4H_8$ | 2.2 |
| 1,3-Butadiene | 0 |
| Aromatic compounds | 0 |
| Others | 23.1 |
| Acetaldehyde | 4.5 |
| $CH_4$ | 2.8 |
| CO | 2.6 |

The selectivities of the above table correspond to the following percentages (by weight):

Butanol: 12%
Diethyl ether: 0.3%
Ethylbutanol: 1%
Hexanol: 1.2%
Ethylhexanol: 0.2%
Octanol: 0.1%
Xylene: 0.2%
Acetaldehyde: 1.4%
Crotyl alcohol and isomers: 0%
Hexen-1-ol: 0%
Butanal: 0.2%
Crotonaldehyde: 0%
Hexanal: 0.1%

The formation of CO and methane, markers of the loss of material in the gas-phase hydrogenation, was thus observed. These products are difficult to separate and thus are not economically upgradable.

This hydrogenation was carried out with the same catalyst as example 1 (liquid phase) but this time in the gas phase. It was observed that acetaldehyde (and other aldehydes) is still present at the end of hydrogenation, during a gas-phase hydrogenation. On the other hand, during liquid-phase hydrogenation (example 1), no trace of acetaldehyde was observed (or of other aldehydes). This clearly shows the advantage of working in the liquid phase.

The invention claimed is:

1. A process for the preparation of a mixture (M) comprising at least one alcohol (Aj), said process comprising the following stages:
   i) a stage of oligomerization of at least one alcohol (Ai) in gas phase, resulting in a mixture (A);
   ii) a stage of condensation of said mixture (A), resulting in a gas stream and in a liquid stream corresponding to a condensed mixture (A); and
   iii) a stage of liquid-phase hydrogenation of said condensed mixture (A) to obtain said mixture (M) comprising at least one alcohol (Aj).

2. The process as claimed in claim 1, wherein said stage i) is a dimerization of ethanol.

3. The process as claimed in claim 1, wherein said mixture (M) comprises butanol.

4. The process as claimed in claim 1, wherein said mixture (M) comprises several alcohols (Aj) having a linear or branched alkyl chain comprising m carbon atoms, with m being equal to 2 or being from 2 to 20.

5. The process as claimed in claim 1, wherein said stage i) is carried out in the presence of a catalyst of alkaline earth metal phosphate type.

6. The process as claimed in claim 5, wherein said catalyst is selected from the group consisting of calcium hydroxyapatites.

7. The process as claimed in claim 6, wherein the (Ca+M)/P molar ratio of said calcium hydroxyapatite is from 1.5 to 2, M being a metal.

8. The process as claimed in claim 1, wherein said stage i) is carried out at a temperature of from 100° C. to 500° C.

9. The process as claimed in claim 1, wherein said stage i) is carried out at a pressure of from 0.3 bar to 6 bars absolute.

10. The process as claimed in claim 5, wherein said at least one alcohol (Ai) of stage i) has a flow rate from 1 to 10 g of said at least one alcohol (Ai) per hour and per gram of said catalyst.

11. The process as claimed in claim 1, wherein said liquid-phase hydrogenation stage iii) is carried out in the presence of a metal catalyst selected from the group consisting of Fe, Ni, Co, Cu, Cr, W, Mo, Pd, Pt, Rh and Ru, said metal catalyst being optionally supported.

12. The process as claimed in claim 11, wherein said metal catalyst is immobilized, in the form of grains or extrudates or in the form of a metal foam.

13. The process as claimed in claim 11, wherein said metal catalyst is in the form of fine particles.

14. The process as claimed in claim 1, wherein said liquid-phase hydrogenation stage iii) is carried out at a temperature from 50° C. to 165° C.

15. The process as claimed in claim 1, wherein said liquid-phase hydrogenation stage iii) is carried out at a pressure from 10 bars to 50 bars.

16. The process as claimed in claim 1, wherein said liquid-phase hydrogenation stage iii) is carried out in an isothermal or adiabatic and tubular or multitubular fixed bed reactor; or in a catalyst-coated reactor/exchanger; or in a reactor stirred by a self-suction stirrer; or in an ejector of venturi or tubular type.

17. The process as claimed in claim 1, wherein said condensed mixture (A) is subjected, on conclusion of said stage ii) and before said stage iii), to a stage of separation of said liquid and gas streams, in order to obtain said liquid stream and to remove said gas stream.

18. The process as claimed in claim 1, further comprising on conclusion of said stage iii), successive distillation stages, in order to separate the different alcohols of said mixture (M), and further comprising stages of recycling said at least one alcohol (Ai).

19. The process as claimed in claim 1, wherein said at least one alcohol (Ai), employed in said stage i), present in said condensed mixture (A) and which has not reacted, is separated from said at least one alcohol (Ai) present in said condensed mixture (A) by liquid/liquid separation, prior to carrying out said stage iii).

20. The process as claimed in claim 1, wherein said mixture (M) obtained in said step iii) is devoid of aldehyde entities.

* * * * *